Oct. 5, 1943. J. PARMENTIER Plant Pat. 603
ROSE PLANT
Filed March 18, 1943
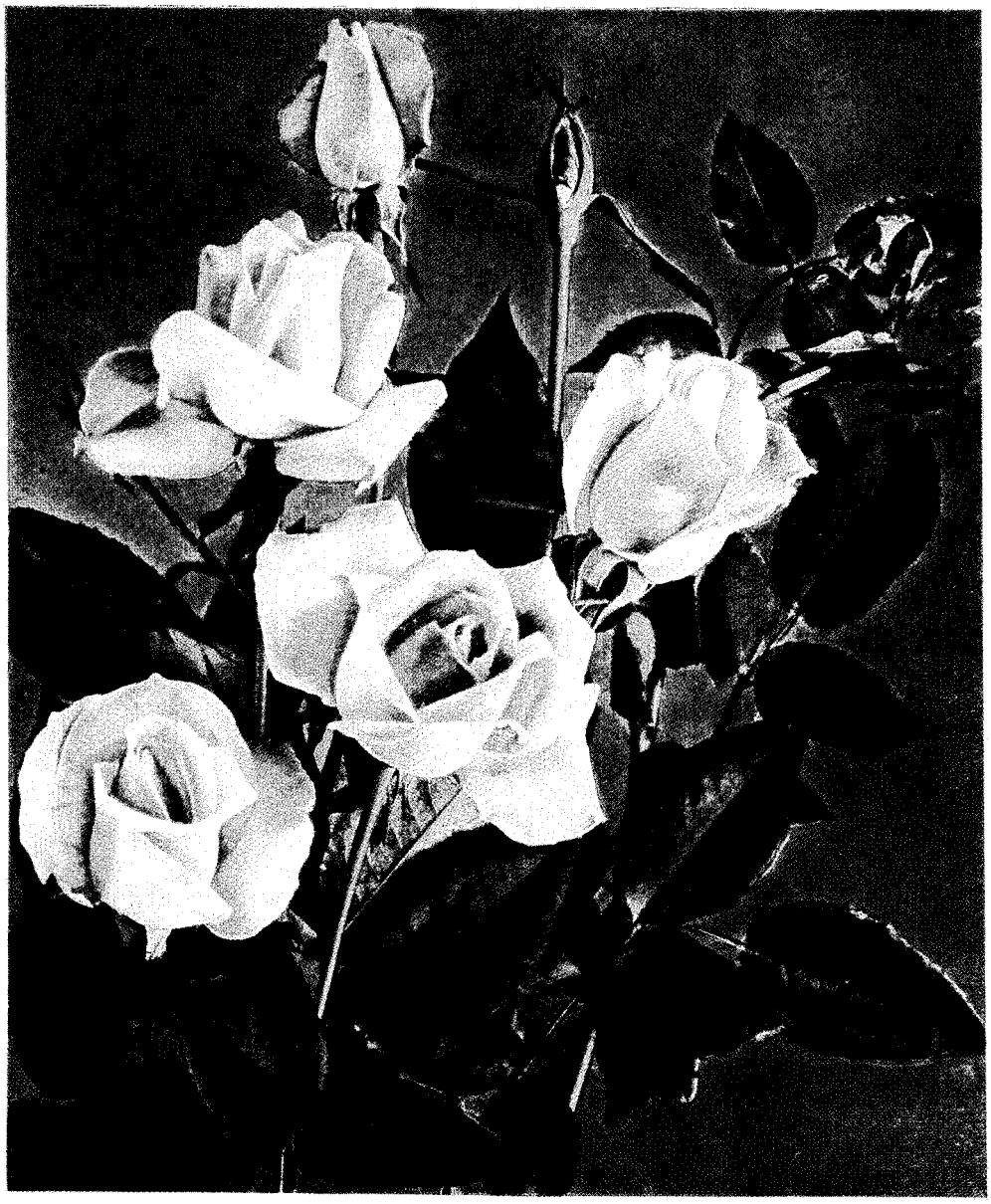
Inventor
John Parmentier
By Robb & Robb
Attorneys Patented Oct. 5, 1943

Plant Pat. 603

UNITED STATES PATENT OFFICE

603

ROSE PLANT

John Parmentier, Bayport, N. Y.

Application March 18, 1943, Serial No. 479,648

1 Claim. (Cl. 47—61)

This discovery relates to a new and distinct variety of hybrid tea rose plant, originating as a sport of "Red Better Times" rose, Plant Patent No. 323.

This new sport was discovered by me growing upon its parent plant in one of my greenhouses and on account of its distinctiveness, I deemed it to be of considerable importance for development for the trade.

Its primary feature of novelty distinguishing it from the parent and other varieties is the clear pink color of the blossoms, and the uniformity of such coloring, viewing the blooms in general tonality from a distance. This color characteristic is all the more outstanding on account of the fact that it does not change, remaining uniform even on cloudy days.

This new variety differs from its parent in other important respects, as will be observed from the following detail description, wherein the color terms are of ordinary dictionary definition except where otherwise designated.

Asexual reproduction of this new variety shows the foregoing characteristics come true to form and are established.

Type: Hardy; tall bush; greenhouse; outdoor; sport; for cut flowers and garden decoration.
Class: Hybrid tea.
Propagation: Holds its distinguishing characteristics through succeeding propagations by cuttings, grafting and budding.

*Flower*

Locality where grown: Bayport, Long Island, New York.
Flowers borne: Singly with two to three side buds to stem; on strong, long stems.
Quantity of bloom: Free; outdoors; in greenhouse.
Continuity: Continuous.
Fragrance: Penetrating; tea.
Bud:
*Peduncle.*—Medium length; erect.
*Before calyx breaks.*—*Size*—medium. *Form*—pointed.
*As calyx breaks.*—Clear Pink, in general tonality.
*As first petal opens.*—*Color*—outside—Soft Pink, in general tonality; inside—Little Darker Pink, in general tonality.
*Color.*—Rose Red, Plate XII, Ridgeway's Color Standard.
Bloom:
*Size.*—When fully open, 4 inches to five inches.
*Petalage.*—Double; from 30 to 35 petals; arranged regularly.
*Form.*—Full, high center; becoming open; petals remaining at first rolled outward; becoming later, at maturity, rolled outward.
Petals: Thick; with inside and outside satiny.
*Shape.*—Oval.

This description was made of a flower grown in a greenhouse during the month of February, 1943, at Bayport, Long Island, New York:

*Color.*—Opening Rose Red, outer petals quickly lightening to tones of Rose color and hues nearly as light as Deep Rose Pink; retains tones of Tyrian Rose on center petals. Petals lighter at base, blending through Deep Rose Pink (all on Plate XII) and Pale Flesh Color (Plate XIV) to Warm Buff (Plate XV) and Antimony Yellow at point of attachment.
*Behavior.*—Drop off cleanly; dark cloudy weather does not affect color.
*Flower longevity.*—Cut roses grown in a greenhouse from 6 to 7 days in February, 1943.

*Plant*

Foliage:
*Leaves.*—Compound of five leaflets.
*Color.*—Dark Dull Yellow Green, Plate XXXII, on face; on reverse Pois Green, Plate XLI; edged with Van Dyke Red, Plate XIII, which color also tones mid-rib and petiole.
*Young foliage.*—Yellowish Citrine, Plate XVI, overlaid with Madder Brown, Plate XIII, which is strong at serrated edge. As green becomes darker, reddish tones disappear, except on edge.
Growth:
*Habit.*—Upright.
*Growth.*—Vigorous.
*Canes.*—Heavy.
*Stems.*—Tones of Cress, Light Cress, Absinthe and Kildare Green, Plate XXXI; few prickles; thorns, Light Coral Red, Plate XIII.

I claim:

A new and distinct variety of rose plant of the hybrid tea class, characterized as to novelty primarily by the Clear Pink (Rose) color of its blossoms, the uniformity and persistency of this coloring, greater number of petals than found in the blooms of its parent, and the long lasting quality of the blooms when used as cut flowers, substantially as shown and described.

JOHN PARMENTIER.